United States Patent
Eshoo et al.

(10) Patent No.: US 9,487,807 B2
(45) Date of Patent: Nov. 8, 2016

(54) COMPOSITIONS AND METHODS FOR PRODUCING SINGLE-STRANDED CIRCULAR DNA

(75) Inventors: Mark W. Eshoo, Solana Beach, CA (US); John Picuri, Carlsbad, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 327 days.

(21) Appl. No.: 13/337,811

(22) Filed: Dec. 27, 2011

(65) Prior Publication Data

US 2012/0164691 A1 Jun. 28, 2012

Related U.S. Application Data

(60) Provisional application No. 61/427,421, filed on Dec. 27, 2010.

(51) Int. Cl.
*C12Q 1/68* (2006.01)
*C12P 19/34* (2006.01)
*C12N 15/10* (2006.01)
*C12N 15/66* (2006.01)

(52) U.S. Cl.
CPC ............... *C12P 19/34* (2013.01); *C12N 15/10* (2013.01); *C12N 15/66* (2013.01)

(58) Field of Classification Search
None
See application file for complete search history.

(56) References Cited

U.S. PATENT DOCUMENTS

| 6,420,144 B1 * | 7/2002 | Chen ..................... C12N 15/10 |
| | | 435/440 |
| 8,455,193 B2 * | 6/2013 | Travers et al. ................ 435/6.1 |
| 2003/0108902 A1 | 6/2003 | Abarzua |
| 2009/0298075 A1 | 12/2009 | Travers et al. |

OTHER PUBLICATIONS

International Search Report and Written Opinion for Application No. PCT/US2011/067368, mailed on Apr. 25, 2012, 7 pages.
Lin C.T., et al., "A Cruciform-Dumbbell Model for Inverted Dimer Formation Mediated by Inverted Repeats," Nucleic Acids Research, 1997, vol. 25 (15), pp. 3009-3016.
Wemmer D.E., et al., "Preparation and Melting of Single Strand Circular DNA Loops," Nucleic Acids Research, 1985, vol. 13 (23), pp. 8611-8621.

* cited by examiner

*Primary Examiner* — Stephanie K Mummert
(74) *Attorney, Agent, or Firm* — David A. Casimir; Casimir Jones, S.C.

(57) ABSTRACT

The present invention provides methods, kits, and compositions for producing single-stranded circular DNA by PCR. In particular, hairpin primers are provided, and methods of use thereof to produce single-stranded circular DNA molecules.

17 Claims, 3 Drawing Sheets

A

B

Figure 2 A-C
A
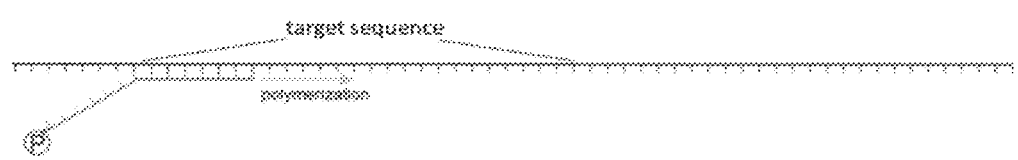
B
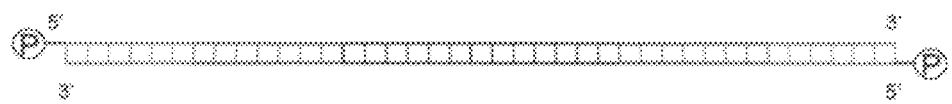
C
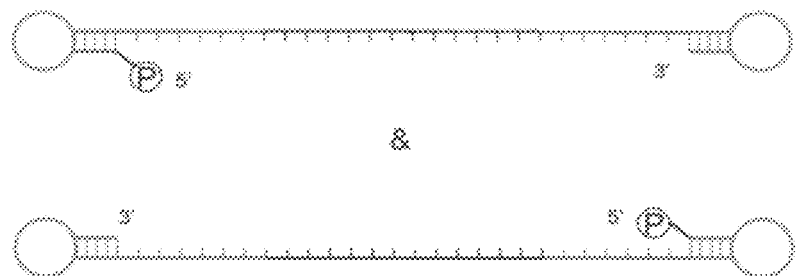

COMPOSITIONS AND METHODS FOR PRODUCING SINGLE-STRANDED CIRCULAR DNA

The present Application claims priority to U.S. Provisional Application Ser. No. 61/427,421 filed Dec. 27, 2010, the entirety of which is incorporated by reference herein.

FIELD OF THE INVENTION

The present invention provides methods, kits, and compositions for producing single-stranded circular DNA by PCR. In particular, hairpin primers are provided, and methods of use thereof to produce single-stranded circular DNA molecules.

BACKGROUND

Single-stranded circular DNA is useful in many areas of biotechnology, both of an experimental as well as commercial nature. One important such use is as a substrate for rolling circle DNA replication, in which a single-stranded circle of DNA is used as a template by a DNA polymerase to produce a long, unbroken single strand of repeating DNA sequence. Single-stranded circular DNAs also find use in single molecule real-time DNA sequencing technologies capable of repeatedly re-sequencing a single piece of double stranded DNA, using a single-stranded circular DNA molecule as template. Single-stranded circular DNAs also find use in microfluidic devices designed to prepare sequence libraries for next-generation sequencing technologies.

Methods for the creation of single-stranded circular DNA molecules have been described (U.S. Pat. No. 7,041,480; WO/2009/120372; National Human Genome Research Institute's "Advanced Sequencing Technology Development Meeting" Stephen Turner, Apr. 1, 2009; "Rapid Library Preparation and Single-molecule (SMRT) Sequencing Enable Same Day Influenza A Genome Sequence Analysis," Poster, AGBT conference, Feb. 24-27, 2010; herein incorporated by reference in their entireties). These methods include ligation of hairpin adapters to the terminal ends of double stranded DNA fragments one wishes to sequence, and ligation of hairpin monomers containing the desired DNA sequence. However, these methods are complex, requiring multiple steps and significant amounts of time (e.g. multiple hours). What is needed are simple, rapid, and efficient PCR methods to produce single-stranded circular DNA from a target sequence of interest.

SUMMARY OF THE INVENTION

In some embodiments, the present invention provides methods of producing single-stranded circular DNA molecules comprising the steps of: (a) annealing a pair of hairpin primers to a target nucleic acid, wherein the hairpin primers comprise a target hybridization region complementary to a sequence of the target nucleic acid, wherein the hairpin primers are configured to hybridize to different ends of the target nucleic acid, and wherein the hairpin primers comprise a hairpin-forming region capable of folding back on itself to form an intramolecular hairpin; (b) amplifying the target nucleic acid with the hairpin primers to produce a duplex of amplicon sequences, wherein the amplicon sequences comprise target sequence flanked on both ends by hairpin primer sequences; (c) altering the solution conditions to promote denaturation of the duplex and formation of the intramolecular hairpins; (d) treating the amplicons with non-strand displacing polymerase to extend amplicon sequence and ligase to unite the 5' and 3' ends of the extended sequence. In some embodiments, the target nucleic acid comprises DNA. In some embodiments, amplifying is by polymerase chain reaction. In some embodiments, altering the solution conditions comprises the steps of: (i) applying denaturing conditions; (ii) altering the solution conditions to favor intramolecular interactions over intermolecular interactions; and (iii) applying reannealing conditions. In some embodiments, denaturing conditions comprise heating above the $T_m$ of the duplex. In some embodiments, solution conditions that favor intramolecular interactions over intermolecular interactions comprise more dilute conditions. In some embodiments, reannealing conditions are reached by cooling (e.g., controlled cooling) below the $T_m$ of the intramolecular hairpins. In some embodiments, the non-strand displacing polymerase comprises a DNA polymerase. In some embodiments, the non-strand displacing polymerase lacks 5' to 3' exonuclease activity. In some embodiments, the non-strand displacing polymerase comprises T4 or T7 DNA polymerase. In some embodiments, the non-strand displacing polymerase extends the amplicon sequence from the 3' end of the hairpin primer until the extended 3' end reaches the 5' end of the other hairpin primer, using the target-hybridization regions of the hairpin primers and the target sequence as a template. In some embodiments, the ligase comprises a DNA ligase. In some embodiments, the ligase comprises T4, *T. aquaticus*, or *E. coli* DNA ligase. In some embodiments, the ligase repairs the nick between the 3' end and the 5' end of the extended sequence.

In some embodiments, the present invention provides compositions and systems comprising: a) a target nucleic acid, and b) a pair of hairpin primers, wherein the hairpin primers comprise a target-hybridization region complementary to a sequence of the target nucleic acid, wherein said hairpin primers are configured to hybridize to opposing strands at different ends of the target nucleic acid in such a manner as to prime polymerization along each strand, and wherein the hairpin primers comprise a hairpin-forming region capable of folding back on itself to form an intramolecular hairpin. In certain embodiments, the systems and compositions further comprise at least one reagent selected from the group consisting of: a polymerase (e.g., a strand displacing polymerase), a non-strand displacing polymerase, and ligase; or all of the recited reagents.

In some embodiments, the present invention provides kits comprising reagents for producing single-stranded circular DNA molecules using the methods described herein. In some embodiments, reagents for producing single-stranded circular DNA molecules comprise hairpin primers. In some embodiments, hairpin primers comprise a target-hybridization region and a hairpin-forming region.

BRIEF DESCRIPTION OF THE DRAWINGS

The summary and detailed description is better understood when read in conjunction with the accompanying drawings which are included by way of example and not by way of limitation.

DEFINITIONS

Figure 1:
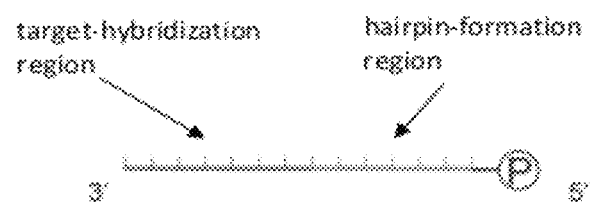
FIG. 1 shows a schematic of a hairpin primer (a) above the $T_m$ of the hairpin-forming region, and (b) below the $T_m$ of the hairpin-forming region.
Figure 1:
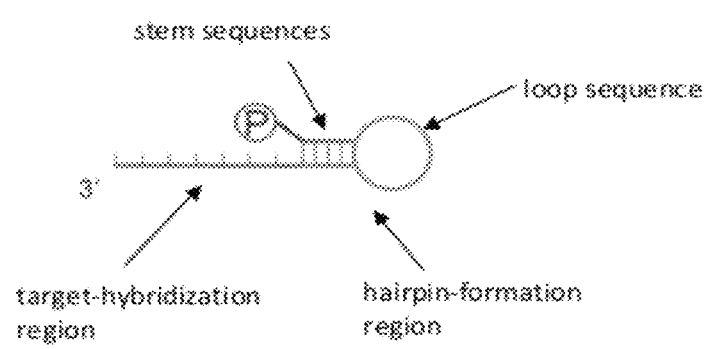

As used herein, the term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method. Primers may include varying degrees of internal secondary structure including, but not limited to, the ability to form intramolecular hairpins.

DETAILED DESCRIPTION

The present invention provides methods, kits, and compositions for producing single-stranded circular nucleic acid (e.g. DNA) by PCR. In particular, hairpin primers are provided, and methods of use thereof to produce single-stranded circular DNA molecules containing target sequences.

In some embodiments, the present invention provides rapid and simple to perform methods to create single-stranded circular DNA molecules containing a PCR product of interest. In some embodiments, PCR primers containing DNA hairpin structures are used in PCR to target a region of interest. In some embodiments, a denaturing step (e.g. heating) is performed to separate the two strands of the PCR product. In some embodiments, the sample is then diluted to encourage intramolecular interactions (e.g., hairpin formation), and the hairpin primers are allowed to self-anneal to produce hairpins at either end of the single-stranded amplicon. Then, addition of a non-strand displacing polymerase (e.g., T4 or T7 polymerase) fills in the DNA between hairpins, and a ligase (e.g., E. coli, Taq, or T4 ligase) seals the nick between the polymerase extended DNA and the other hairpin primer. In some embodiments, this process creates single-stranded circular DNA molecules (e.g., for use in a number of technologies such as DNA sequencing and rolling circle amplification).

In some embodiments the present invention provides compositions (e.g. hairpin primers) and methods for synthesis of single-stranded circular DNA containing a target sequence. In some embodiments, single-stranded circular DNA synthesis comprises one or more of the steps of: primer annealing, DNA polymerization, amplicon denaturation, hairpin formation, non-strand displacing DNA polymerization, and ligation.

Figure 2:
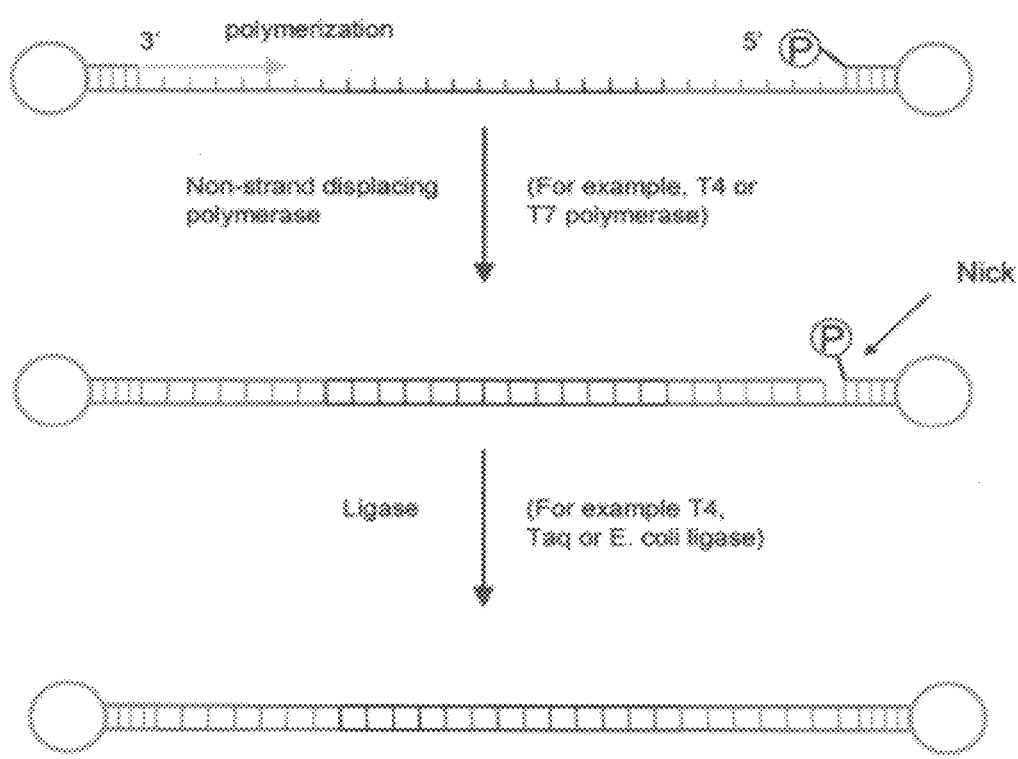
FIG. 2 shows a schematic of (a) nucleic acid polymerization on a target template, primed by a hairpin primer; (b) the majority product resulting from successive rounds of target amplification using hairpin primers flanking a target region; (c) the majority amplification product following denaturing, possible dilution, and re-annealing; and (d) completion of polymerization of the single-stranded DNA molecule, and ligation of the nick to complete the single-stranded circle.

In some embodiments, a target nucleic acid sequence (e.g. DNA sequence) is selected for incorporation into a single-stranded circular DNA molecule. In some embodiments, hairpin primers are designed flanking the target sequence. In some embodiments, each hairpin primer comprises a target-hybridization region complementary to a terminal portion of the target sequence. In some embodiments, each hairpin primer comprises a hairpin-forming region that is not complementary to the target sequence, but is capable of folding back upon itself to form an intramolecular stem-loop within the hairpin-forming region. In some embodiments, the target sequence is amplified using the hairpin primers to initiate nucleic acid polymerization (e.g. DNA polymerization) (SEE FIG. 2). In some embodiments, after multiple cycles of amplification (e.g. PCR), the majority product is a double-stranded linear DNA molecule flanked by the hairpin primers (SEE FIG. 2B). In some embodiments, because the newly polymerized DNA acts as the template for successive rounds of amplification, the hairpin-forming region, which is not complementary to the original target sequence, is incorporated into the resulting amplicon (SEE FIG. 2B). In some embodiments, the amplification products are subjected to denaturing conditions (e.g. heat, denaturant, etc.) to denature the double stranded product, thereby separating the two strands, resulting in two single-stranded amplification products. In some embodiments, while the amplicons are denatured, solution conditions are adjusted to promote intramolecular interactions (e.g. hairpin formation) over intermolecular interactions (e.g. duplex formation). In some embodiments, adjusting solution conditions comprises increasing the volume of the solution or altering the salt concentration. In some embodiments, solution conditions are re-adjusted to promote annealing of the hairpin-forming regions of the primers. In some embodiments, the denaturing, and annealing steps promote disassociation of the stands of the product duplex and formation of single-stranded products flanked by hairpin structures (SEE FIG. 2C). In some embodiments, a non-strand displacing polymerase (e.g., T4 polymerase, T7 polymerase, etc.) is added to the reaction solution. In some embodiments, the solution is brought under conditions suitable for polymerization, and the polymerase synthesizes a strand complementary to the target-hybridizing region of the primers and the target sequence, using the 3' end of the hairpin-forming region as a primer (SEE FIG. 2D). In some embodiments, a ligase (e.g., T4 ligase, E. coli ligase, etc.) is added to the solution to close the gap in the nucleic acid sequence between the 3' end of the newly polymerized nucleic acid and the 5' terminal phosphate of the hairpin-forming region of the primer (SEE FIG. 2D). In some embodiments, upon closing of the nick, a single-stranded circular nucleic acid (e.g. DNA) is produced.

In some embodiments, the present invention provides compositions and method for the amplification of nucleic acids (e.g. DNA, RNA, etc.). In some embodiments, the present invention provides all the reagents necessary for nucleic acid amplification (e.g. primers, polymerase, deoxynucleotides, template, buffer, etc.). In some embodiments, an amplification reaction is any reaction in which nucleic acid replication occurs repeatedly over time to form multiple copies of at least one segment of a template or target nucleic acid molecule (e.g. DNA, RNA). In some embodiments, amplification generates an exponential or linear increase in the number of copies of the template nucleic acid. Amplifications may produce in excess of a 1.000-fold increase in template copy-number and/or target-detection signal. Exemplary amplification reactions include, but are not limited to those that utilize thermal cycling to produce multiple rounds of nucleic acid amplification, including, but not limited to polymerase chain reaction (PCR) or ligase chain reaction (LCR). Alternative amplification reactions, which may be performed isothermally, may also find use herein, such as branched-probe DNA assays, cascade-RCA, helicase-dependent amplification, loop-mediated isothermal amplification (LAMP), nucleic acid based amplification (NASBA), nicking enzyme amplification reaction (NEAR), PAN-AC, Q-beta replicase amplification, rolling circle replication (RCA), self-sustaining sequence replication, strand-displacement amplification, and the like.

Amplification may be performed with any suitable reagents (e.g. template nucleic acid (e.g. DNA or RNA), primers, probes, buffers, replication catalyzing enzyme (e.g. DNA polymerase, RNA polymerase), nucleotides, salts (e.g. $MgCl_2$), etc. In some embodiments, an amplification mixture includes any combination of at least one primer or primer pair, at least one probe, at least one replication enzyme (e.g., at least one polymerase, such as at least one DNA and/or RNA polymerase), and deoxynucleotide (and/or nucleotide) triphosphates (dNTPs and/or NTPs), etc.

In some embodiments, the present invention utilizes nucleic acid amplification that relies on alternating cycles of heating and cooling (i.e., thermal cycling) to achieve successive rounds of replication (e.g., PCR). In some embodiments, PCR is used to amplify target nucleic acids. PCR may be performed by thermal cycling between two or more temperature set points, such as a higher melting (denaturation) temperature and a lower annealing/extension temperature, or among three or more temperature set points, such as a higher melting temperature, a lower annealing temperature, and an intermediate extension temperature, among others. PCR may be performed with a thermostable polymerase, such as Taq DNA polymerase (e.g., wild-type enzyme, a Stoffel fragment, FastStart polymerase, etc.), Pfu DNA polymerase, S-Tbr polymerase, Tth polymerase, Vent polymerase, or a combination thereof, among others. Typical PCR methods produce an exponential increase in the amount of a product amplicon over successive cycles, although linear PCR methods also find use in the present invention.

In some embodiments, any suitable PCR methodology, combination of PCR methodologies, or combination of amplification techniques may be utilized in the partitioned methods disclosed herein, such as conventional PCR, allele-specific PCR, assembly PCR, asymmetric PCR, digital PCR, endpoint PCR, hot-start PCR, in situ PCR, intersequence-specific PCR, inverse PCR, linear after exponential PCR, ligation-mediated PCR, methylation-specific PCR, mini-primer PCR, multiplex ligation-dependent probe amplification, multiplex PCR, nested PCR, overlap-extension PCR, polymerase cycling assembly, qualitative PCR, quantitative PCR, real-time PCR, RT-PCR, single-cell PCR, solid-phase PCR, thermal asymmetric interlaced PCR, touchdown PCR, universal fast walking PCR, etc.

In some embodiments, the present invention provides primers for use in nucleic acid amplification (e.g., PCR). Primers according to this invention are short oligonucleotides, generally under fifty bases in length that hybridize to a target strand and are extended by an appropriate polymerase. A primer may be composed of naturally occurring nucleotides, or it may include non-natural nucleotides and non-natural internucleotide linkages. In some embodiments, primers include secondary structure elements (e.g. hairpins, stem-loops, pseudoknots, etc.; See, for example, Nazarenko I A, Bhatnagar S K, Hohman R J (1997) Nucleic Acids Res. 25:2516-2521.; herein incorporated by reference in its entirety). In some embodiments, amplifications include use of one or more primer pairs each consisting of a forward primer and a reverse primer. In some embodiments, both the forward and reverse primer are hairpin primers.

In methods, kits and oligonucleotide sets according to this invention, either one primer of a pair or both primers of the pair may be labeled with a covalently bound fluorophore that fluoresces when nearby fluorescent DNA dye is stimulated. When the labeled primer hybridizes (or anneals) to its complementary sequence in a template strand, a double-stranded region is formed. Fluorescent DNA dye associates with that region, by intercalating therein or otherwise, and becomes fluorescent in that region, which is nearby to the primer's fluorophore such that when the dye is stimulated at a wavelength that does not directly excite the fluorophore, the fluorophore emits at its characteristic wavelength. These primers may be used to monitor synthesis of products resulting by extension of a DNA polymerase such as those resulting from PCR and primer extension assays in real-time or by end-point detection and/or to assess product specificity by melting curve analysis.

In some embodiments, primers according to this invention, are used as substrates for extension by a DNA polymerase, including primers for PCR amplification. In some embodiments, primers of the present invention contain a target-hybridization region, a hairpin-forming region, and a 5' terminal phosphate (SEE FIG. 1). When the primers are brought above the melting temperature of the hairpin-forming sequence, they resemble a conventional primer, lacking secondary structure (SEE FIG. 1A). When the primers are below the melting temperature of the hairpin-forming sequence, the primer folds back on itself, forming an intramolecular stem-loop structure within the hairpin-forming region (SEE FIG. 1B). In some embodiments, hairpin formation is limited to the hairpin-forming region.

In some embodiments, a primer is of any length suitable for initiating (e.g. priming) nucleic acid polymerization (e.g. <100 nucleotides, <50 nucleotides, <40 nucleotides, <30 nucleotides, <20 nucleotides, >10 nucleotides, >20 nucleotides, etc.). In some embodiments, the target-hybridization region of a primer is of any length suitable for initiating (e.g. priming) nucleic acid polymerization (e.g. <100 nucleotides, <50 nucleotides, <40 nucleotides, <30 nucleotides, <20 nucleotides, >10 nucleotides, >20 nucleotides, etc.). In some embodiments, the hairpin-forming region of a primer is of any suitable length to form an intramolecular hairpin structure without interfering with hybridization of the target-hybridization region to the target sequence (e.g. <100 nucleotides, <50 nucleotides, <40 nucleotides, <30 nucleotides, <20 nucleotides, >10 nucleotides, >20 nucleotides, >30 nucleotides, >40 nucleotides, etc.).

In some embodiments, the hairpin-forming region of a primer comprises two stem sequences and a loop sequence. In some embodiments, the two stem sequences are complementary to each other, or exhibit a significant degree of complementarity (e.g., 100% complementary . . . 98% complementary . . . 95% complementary . . . 90% complementary . . . 85% complementary . . . 80% complementary . . . 75% complementary . . . 70% complementary, etc.). In some embodiments, the loop sequence of the hairpin-forming region is not complementary or does not exhibit significant complementarity to other regions of the primer. In some embodiments, the loop sequence is at least three bases in length (e.g. 3, 4, 5, 6, 7, 8, 9, 10, 20, etc.). In some embodiments, the loop sequence is 4-8 bases in length (e.g. 4, 5, 6, 7, 8). In some embodiments, a loop sequence is stabilized by intra-loop interactions (e.g. base stacking). In some embodiments, the loop sequence is sequence known in the art to form stable loops (e.g. UUCG, GNRA, GGGG, etc.). In some embodiments, a loop is random sequence, or pseudorandom sequence between the two stem sequences. In some embodiments, the stem sequences and loop sequence are selected to provide a suitable hairpin melting temperature ($T_m$) for use with embodiments of the present invention. In some embodiments, the $T_m$ of the hairpin-forming region is affected by one or more of: the length of the stem sequences, GC-content of stem sequences, complementarity of stem sequences, length of loop sequence, sequence of loop sequence, and other factors known to those of skill in the art. In some embodiments, the $T_m$ of the hairpin is below the extension temperature of the amplification reaction it is designed to prime, so the hairpin does not interfere with the reaction. In some embodiments, the $T_m$ of the hairpin is below the annealing temperature of the amplification reaction it is designed to prime, so the hairpin does not interfere with the reaction. In some embodiments, the $T_m$ of the hairpin is above either the annealing temperature or the extension temperature of the amplification reaction it is designed to prime, but the hairpin is designed not to physically interfere with priming of the amplification reaction.

In some embodiments, the present invention provides compositions and methods for the production of single-stranded circular DNA from a target sequence. In some embodiments, a target nucleic acid (e.g. DNA) is of any length suitable for PCR amplification. In some embodiments, the target sequence is from any suitable source of nucleic acids. In some embodiments, target-containing nucleic acids are derived from any suitable source, and for purposes related to any field, including but not limited to diagnostics, research, medicine, forensics, epidemiology, pathology, archaeology, etc. Nucleic acid sources may be biological, synthetic, environmental, forensic, veterinary, clinical, etc. in origin. In some embodiments, target-containing nucleic acids are derived from any suitable source, including eukaryotes, prokaryotes (e.g. infectious bacteria), mammals, humans, non-human primates, canines, felines, bovines, equines, porcines, mice, viruses, etc. Nucleic acid sources may contain, e.g., whole organisms, organs, tissues, cells, organelles (e.g., chloroplasts, mitochondria), synthetic nucleic acid, cell lysate, etc. Target-containing nucleic acids may be of any type, e.g., genomic DNA, RNA, plasmids, bacteriophages, synthetic origin, natural origin, and/or artificial sequences (non-naturally occurring), synthetically-produced but naturally occurring sequences, etc. Target-containing nucleic acids may be derived from biological samples, including, for example, whole blood, lymphatic fluid, serum, plasma, sweat, tear, saliva, sputum, cerebrospinal (CSF) fluids, amniotic fluid, seminal fluid, vaginal excretions, serous fluid, synovial fluid, pericardial fluid, peritoneal fluid, pleural fluid, transudates, exudates, cystic fluid, bile, urine, gastric fluids, intestinal fluids, fecal samples, and swabs or washes (e.g., oral, nasopharangeal, optic, rectal, intestinal, vaginal, epidermal, etc.) and/or other biological specimens.

EXPERIMENTAL

Example 1

Generation of Single-Stranded Circular DNA Using a Hairpin PCR Primer

Hairpin PCR primers are designed to amplify a target of interest. A reaction solution is prepared by combining: a nucleic acid containing the target DNA sequence, hairpin PCR primers, an appropriate thermostable polymerase (Taq, Pfu, etc.), and dNTPs in an appropriate buffer containing the appropriate salts and at the appropriate pH for the selected polymerase. The reaction solution is cycled through denaturation, annealing, and extension temperatures (e.g., 95° C., 55° C., 70° C.) for an appropriate amount of time, and suitable number of rounds to achieve PCR amplification.

Subsequently, reaction solution is heated (e.g., 95° C. for 10 minutes) to denature the double stranded PCR products, and cooled to allow for the hairpin to form. Diluting the PCR reaction products or controlling the speed of cooling can be used to drive the reaction towards the desired intramolecular hairpin products and away from the unwanted intermolecular double stranded PCR product. After this denaturing and annealing, a non-strand displacing polymerase with no 5' to 3' exonuclease activity (e.g., T4 or T7 polymerase) is added to the reaction solution along with more dNTPs if needed. After an appropriate amount of polymerization time, a ligase (e.g. T4, *T. aquaticus* or *E. coli*) is added along with the appropriate cofactors (e.g., rATP or NAD+). In some embodiments, the ligase could also potentially be included with the non-strand displacing polymerase, thereby combining the two steps.

A combination of appropriate exonuclease treatment (e.g., exo III and exo VII), gel electrophoresis, and mass spectrometry is used to test for the successful creation of the single-stranded circular DNA molecules.

Although the invention has been described in connection with specific preferred embodiments, it should be understood that the invention as claimed should not be unduly limited to such specific embodiments. Various modification and variation of the described methods and compositions of the invention will be apparent to those skilled in the art without departing from the scope and spirit of the invention. Indeed, various modifications of the described modes for carrying out the invention understood by those skilled in the relevant fields are intended to be within the scope of the following claims. All publications and patents mentioned in the present application and/or listed below are herein incorporated by reference.

We claim:

1. A method of producing single-stranded circular DNA molecules comprising the steps of:
   (a) annealing a pair of hairpin primers to a target nucleic acid, wherein said hairpin primers comprise a target-hybridization region complementary to a sequence of said target nucleic acid, wherein said hairpin primers are configured to hybridize to opposing strands at different ends of said target nucleic acid in such a manner as to prime polymerization along each strand, wherein said hairpin primers comprise a hairpin-forming region capable of folding back on itself to form an intramolecular hairpin and wherein at least one primer of said pair of hairpin primers comprises a 5' terminal phosphate in the hairpin-forming region of said primer;

(b) amplifying said target nucleic acid with said pair of hairpin primers to produce a duplex of amplicon sequences, wherein said amplicon sequences comprise target sequence flanked on both ends by hairpin primer sequences wherein said hairpin primer sequences form hairpin sequences;

(c) altering the solution conditions to promote denaturation of said duplex and formation of said intramolecular hairpins; and (d) treating said amplicons with non-strand displacing polymerase to extend amplicon sequence and ligase to unite the 5' and 3' ends of the extended sequence.

2. The method of claim 1, wherein said target nucleic acid comprises DNA.

3. The method of claim 1, wherein said amplifying is by polymerase chain reaction.

4. The method of claim 1, wherein altering the solution conditions comprises the steps of:
 (i) applying denaturing conditions;
 (ii) altering said solution conditions to favor intramolecular interactions over intermolecular interactions; and
 (iii) applying reannealing condition.

5. The method of claim 4, wherein denaturing conditions comprise heating above the $T_m$ of said duplex.

6. The method of claim 4, wherein solution conditions that favor intramolecular interactions over intermolecular interactions comprise more dilute conditions.

7. The method of claim 4, wherein reannealing conditions comprise controlled cooling below the $T_m$ of said intramolecular hairpins.

8. The method of claim 1, wherein said non-strand displacing polymerase comprises a DNA polymerase.

9. The method of claim 8, wherein said non-strand displacing polymerase lacks 5' to 3' exonuclease activity.

10. The method of claim 9, wherein said non-strand displacing polymerase comprises T4 or T7 DNA polymerase.

11. The method of claim 1, wherein said non-strand displacing polymerase extends the amplicon sequence from the 3' end of the hairpin primer until the extended 3' end reaches the 5' end of the other hairpin primer, using the target-hybridization regions of the hairpin primers and the target sequence as a template.

12. The method of claim 1, wherein said ligase comprises a DNA ligase.

13. The method of claim 12, wherein said ligase comprises T4, *T. aquaticus*, or *E. coli* DNA ligase.

14. The method of claim 1, wherein said ligase repairs the nick between the 3' end and the 5' end of said extended sequence.

15. A method of producing single-stranded circular DNA molecules comprising the steps of:

(a) annealing a pair of hairpin primers to a target nucleic acid wherein said target nucleic acid comprises DNA, wherein said hairpin primers comprise a target-hybridization region complementary to a sequence of said target nucleic acid, wherein said hairpin primers are configured to hybridize to opposing strands at different ends of said target nucleic acid in such a manner as to prime polymerization along each strand, wherein said hairpin primers comprise a hairpin-forming region capable of folding back on itself to form an intramolecular hairpin, and wherein at least one primer of said pair of hairpin primers comprises a 5' terminal phosphate in the hairpin-forming region of said primer;

(b) amplifying said target nucleic acid with said pair of hairpin primers to produce a duplex of amplicon sequences, wherein said amplicon sequences comprise target sequence flanked on both ends by hairpin primer sequences wherein said hairpin primer sequences form hairpin sequences, and wherein said amplifying is by polymerase chain reaction;

(c) altering the solution conditions to promote denaturation of said duplex and formation of said intramolecular hairpins wherein said altering the solution conditions comprises the steps of:
 (i) applying denaturing conditions wherein said denaturing conditions comprise heating above the $T_m$ of said duplex;
 (ii) altering said solution conditions to favor intramolecular interactions over intermolecular interactions wherein said solution conditions that favor intramolecular interactions over intermolecular interactions comprise more dilute conditions; and
 (iii) applying reannealing conditions wherein said reannealing conditions comprise controlled cooling below the $T_m$ of said intramolecular hairpins;

(d) treating said amplicons with non-strand displacing polymerase to extend amplicon sequence and ligase to unite the 5' and 3' ends of the extended sequence wherein said non-strand displacing polymerase comprises a DNA polymerase, wherein said non-strand displacing polymerase lacks 5' to 3' exonuclease activity, wherein said non-strand displacing polymerase comprises T4 or T7 DNA polymerase, and wherein said non-strand displacing polymerase extends the amplicon sequence from the 3' end of the hairpin primer until the extended 3' end reaches the 5' end of the other hairpin primer using the target-hybridization regions of the hairpin primers and the target sequence as a template, wherein said ligase comprises a DNA ligase selected from the group consisting of T4, *T. aquaticus*, or *E. coli* DNA ligase, and wherein said ligase repairs the nick between the 3' end and the 5' end of said extended sequence; and (e) testing for successful creation of said single-stranded circular DNA molecules.

16. The method of claim 15, wherein said testing comprises exonuclease treatment, gel electrophoresis, and mass spectrometry.

17. The method of claim 16 wherein said exonuclease treatment comprises exo III and/or exo VII treatment.

* * * * *